United States Patent
Golden

(10) Patent No.: US 9,687,315 B2
(45) Date of Patent: Jun. 27, 2017

(54) DENTAL PLIER DESIGN WITH OFFSETTING JAW AND PAD ELEMENTS FOR ASSISTING IN REMOVING UPPER AND LOWER TEETH UTILIZING THE DENTAL PLIER DESIGN

(75) Inventor: Richard Golden, Detroit, MI (US)

(73) Assignee: Beak and Bumper, LLC, Detroit, MI (US)

( * ) Notice: Subject to any disclaimer, the term of this patent is extended or adjusted under 35 U.S.C. 154(b) by 884 days.

(21) Appl. No.: 13/571,784

(22) Filed: Aug. 10, 2012

(65) Prior Publication Data

US 2013/0022939 A1 Jan. 24, 2013

Related U.S. Application Data

(63) Continuation-in-part of application No. 11/095,355, filed on Mar. 31, 2005, which is a continuation-in-part of application No. 10/306,115, filed on Nov. 27, 2002, now Pat. No. 6,910,890.

(51) Int. Cl.
*A61C 3/14* (2006.01)

(52) U.S. Cl.
CPC ...................................... *A61C 3/14* (2013.01)

(58) Field of Classification Search
CPC ...................................................... A61C 3/14
USPC ........................................ 433/3–4, 157, 159
See application file for complete search history.

(56) References Cited

U.S. PATENT DOCUMENTS

| 4,261 A | 11/1845 | Baker |
|---|---|---|
| 75,716 A | 3/1868 | Woolverton |
| 97,399 A | 11/1869 | Holmes |
| 145,058 A | 12/1873 | French |
| 354,863 A | 12/1886 | Hughes |
| 390,561 A | 10/1888 | Brown |

(Continued)

FOREIGN PATENT DOCUMENTS

| CA | 2492576 A1 | 7/2006 |
|---|---|---|
| KR | 200270833 Y1 | 4/2002 |

(Continued)

OTHER PUBLICATIONS

Bennion, Antique Dental Instruments, 1986, Chapter 2, pp. 29-38, Sotheby's Publications, London.

(Continued)

*Primary Examiner* — Cris L Rodriguez
*Assistant Examiner* — Hao D Mai
(74) *Attorney, Agent, or Firm* — Dinsmore & Shohl LLP

(57) ABSTRACT

A dental pliers and method for loosening teeth from an underlying bone and gum. Pivotally connected handles which each include a user grasping portion. The first handle terminates in an arcuately extending beak exhibiting a narrowed blade edge. The second handle terminates in an opposing pad support with an ergonomic configuration substantially matching that of the patient's gum line. Upon positioning the support along a buccal location at or below the gum line, and upon aligning the beak in abutting fashion against a lingual surface of a tooth, the pad support defines a center point of rotation proximate to an edge location of the gum line and bone. The handles are subsequently rotated in an outward fashion away from the patient's gum line to separate the tooth and its roots from the patient's gum line and bone.

5 Claims, 6 Drawing Sheets

(56) References Cited

U.S. PATENT DOCUMENTS

| | | |
|---|---|---|
| 478,217 A | 7/1892 | Blake, Sr. |
| 491,519 A | 2/1893 | Blake, Sr. |
| 491,932 A | 2/1893 | Whitlock |
| 536,166 A | 3/1895 | Angie |
| 553,718 A | 1/1896 | Monfort |
| 610,840 A | 9/1898 | Angie |
| 617,587 A | 1/1899 | Link |
| 681,224 A | 8/1901 | Jacob |
| 732,288 A | 6/1903 | Felsch |
| 831,307 A | 9/1906 | Spahn |
| 833,375 A | 10/1906 | Dollar |
| 882,404 A | 3/1908 | Miner |
| 902,570 A | 11/1908 | Ellis |
| 908,056 A | 12/1908 | Whitney et al. |
| 996,030 A | 6/1911 | Parker |
| 1,058,743 A * | 4/1913 | Gilbert .......................... 433/145 |
| 1,276,274 A | 8/1918 | Shaffer |
| 1,395,714 A | 11/1921 | Johnson |
| 1,399,265 A | 12/1921 | Lay |
| 1,626,226 A | 4/1927 | Cantor |
| 1,628,499 A | 5/1927 | Joesch |
| 1,674,485 A | 6/1928 | Smith |
| 1,675,815 A | 7/1928 | Miller |
| 1,678,313 A | 7/1928 | Atkinson |
| 1,782,364 A | 11/1930 | Nation |
| 1,866,771 A | 7/1932 | Johnson |
| 2,030,798 A | 2/1936 | Krajeski |
| 2,212,801 A | 8/1940 | Torbert |
| D145,058 S | 6/1946 | French |
| 2,428,689 A | 10/1947 | Sykes |
| 2,430,271 A | 11/1947 | Brantley |
| 2,497,254 A | 2/1950 | Brantley |
| 2,504,227 A | 4/1950 | Rubba |
| 2,507,784 A | 5/1950 | Hamel |
| 2,563,920 A | 8/1951 | Christensen |
| 2,592,641 A | 4/1952 | Balderstone |
| 2,698,483 A | 1/1955 | Berkowitz |
| 2,944,341 A | 7/1960 | Lane |
| 3,017,692 A | 1/1962 | Floyd |
| 3,456,349 A | 7/1969 | Heimann |
| 3,468,031 A | 9/1969 | Mumaw |
| 3,644,998 A | 2/1972 | Rubino |
| 3,685,097 A | 8/1972 | Scott et al. |
| 3,834,026 A | 9/1974 | Klein |
| 3,866,324 A | 2/1975 | Walser |
| 3,898,738 A | 8/1975 | Linder |
| 4,014,226 A | 3/1977 | Karamarkovich |
| 4,028,969 A | 6/1977 | Politte |
| 4,031,624 A | 6/1977 | Heimann |
| RE29,889 E | 1/1979 | Klein |
| D253,088 S | 10/1979 | Levin |
| 4,230,454 A | 10/1980 | Lococo et al. |
| 4,443,196 A | 4/1984 | Rico |
| 4,559,853 A | 12/1985 | Oye |
| 4,609,353 A | 9/1986 | Kline |
| D296,822 S | 7/1988 | Fenton |
| 5,044,954 A | 9/1991 | Lukase et al. |
| 5,057,016 A | 10/1991 | Lukase et al. |
| 5,122,058 A | 6/1992 | Lukase et al. |
| 5,205,734 A | 4/1993 | Marangoni et al. |
| D335,249 S | 5/1993 | Hopkins |
| 5,368,600 A | 11/1994 | Failla et al. |
| D362,293 S | 9/1995 | Formaggioni |
| D370,161 S | 5/1996 | Snyder |
| 5,538,421 A | 7/1996 | Aspel |
| D392,167 S | 3/1998 | Cockrell et al. |
| 5,735,857 A | 4/1998 | Lane |
| 5,755,573 A | 5/1998 | LeBlanc |
| D396,619 S | 8/1998 | Hunter |
| 5,833,460 A | 11/1998 | Maeda |
| 5,996,450 A | 12/1999 | St. John |
| 6,042,379 A | 3/2000 | Rodriguez del Val |
| D426,440 S | 6/2000 | Torres |
| 6,210,161 B1 | 4/2001 | Montgomery |
| 6,280,184 B1 | 8/2001 | Hamilton |
| 6,293,790 B1 | 9/2001 | Hilliard |
| 6,345,983 B1 | 2/2002 | Godfrey |
| 6,579,296 B1 | 6/2003 | Macey |
| D490,288 S | 5/2004 | Griffin |
| 6,745,648 B2 | 6/2004 | Stier |
| 6,790,037 B1 | 9/2004 | Orecchia |
| 6,910,890 B2 | 6/2005 | Golden |
| 6,934,991 B2 | 8/2005 | Kinkade |
| 7,021,932 B2 | 4/2006 | Standish |
| 7,128,575 B1 | 10/2006 | Sohn |
| D543,813 S | 6/2007 | Tutorow |
| D561,899 S | 2/2008 | Golden |
| 7,344,375 B2 | 3/2008 | Mukasa et al. |
| D566,840 S | 4/2008 | Golden |
| D567,376 S | 4/2008 | Golden |
| 2002/0146665 A1 | 10/2002 | Tamura |
| 2004/0101805 A1 | 5/2004 | Golden |
| 2004/0152044 A1 | 8/2004 | Khan-Sullman |
| 2004/0159194 A1 | 8/2004 | Ting |
| 2005/0070955 A1 | 3/2005 | Young |
| 2005/0170314 A1 | 8/2005 | Golden |
| 2005/0186536 A1 | 8/2005 | Zepf |
| 2005/0214719 A1 | 9/2005 | Hermann |
| 2006/0166167 A1 | 7/2006 | Syfrig |
| 2008/0187885 A1 | 8/2008 | Golden |
| 2008/0254410 A1 | 10/2008 | Golden |
| 2011/0256502 A1 * | 10/2011 | Katz .............................. 433/114 |

FOREIGN PATENT DOCUMENTS

| | | |
|---|---|---|
| WO | 2008097954 A1 | 8/2008 |
| WO | 2008097961 A1 | 8/2008 |

OTHER PUBLICATIONS

Harris, The Principles and Practice of Dental Surgery, Eight Edition, pp. 361-363, 1863, Lindsay & Blakiston, Philadelphia.

Ring, Dentistry an Illustrated History, Sep. 1985, Abradale Press and Harry N. Abrams, Inc.

Coombs, Eagle Beak molar forceps: evolution and usage, Australian Dental Journal, 1985, pp. 360-363, vol. 30, No. 5.

Instrument Darwinism Sally Dummer traces the evolution of an extraction tool, BDANews, May 2008, p. 22, vol. 21, No. 5.

"A Pictoral History of Dentistry" web page. (Believed to have been offered for sale, publicly used, and/or published prior to the filed of this application.).

Atkinson, Some early dental extraction instruments including the pelican, bird or axe?, Australian Dental Journal, 2002, pp. 90-93, vol. 47, No. 2.

Hayson, The Dental Key: A Dangerous and Barbarous Instrument, Journal of the History of Dentistry, Nov. 2005, pp. 95-96, vol. 53, No. 3.

Wynbrandt, The Excruciating History of Dentistry: Toothsome Tales & Oral Oddities from Babylon to Braces, 1998, pp. 70-71, St. Martin's Press, New York.

Fillebrown, The Use of the Key, the Dental Cosmos, Feb. 1885, pp. 69-74, vol. 27, No. 2.

Busch, Tooth Keys, Journal of the History of Dentistry, Jul. 2003, pp. 57-59, vol. 51, No. 2.

Harn et al., Unusual Instrument Relationship—Wrench or Turnkey, Journal of the History of Dentistry, Mar. 1996, pp. 25-6, vol. 44 No. 1.

Baker & Riley, Lever operated Toothkey, patented 1845, obtained from "http://dmd.co.il/antiques/big_he.html".

* cited by examiner

DENTAL PLIER DESIGN WITH OFFSETTING JAW AND PAD ELEMENTS FOR ASSISTING IN REMOVING UPPER AND LOWER TEETH UTILIZING THE DENTAL PLIER DESIGN

CROSS-REFERENCE TO RELATED APPLICATIONS

This Application is a Continuation-in-part of application Ser. No. 11/095,355 filed on Mar. 31, 2005, which is in turn a Continuation-in-part of application Ser. No. 10/306,115 filed on Nov. 27, 2002, now U.S. Pat. No. 6,910,890, the contents of which are incorporated herein.

FIELD OF THE INVENTION

The present invention teaches a lever type dental forceps for loosening teeth prior to conventional linear extraction and which incorporates a first jaw portion and a second and offsetting support pad. In operation, the lever type dental forceps enables a rotating, rather than a pulling, force to be exerted against a tooth in order to more quickly and efficiently loosen the tooth from the underlying bone without damage to the bone and/or fracturing of the root tip.

BACKGROUND OF THE INVENTION

The prior art is documented with various types of dental appliances, including such as pliers or forceps, utilized in the removal of teeth. By design, these often include first and second handles terminating at forward most locations in pivotally adjustable gripping locations which are applied to opposite surfaces of the tooth, upon which a linear extracting force is applied. Shortcomings of such dental appliances include time and energy inefficiencies associated with such linear extracting techniques, combined with higher incidences of fracture of the root tip from the tooth.

SUMMARY OF THE INVENTION

The present invention discloses a dental pliers appliance, as well as an associated method, for loosening teeth from the jaw bone and gum of the dental patient, and which enables the tooth to be subsequently linearly extracted though the use of a conventional dental forceps or other known linear retracting instrument, with little or no extracting force being expended by the user. As stated previously, advantages associated with the appliance include the substitution of an exerting and linear extracting force with a much more controlled rotating or lever-style motion which is applied to a selected tooth or embedded root, and in order to more quickly and efficiently loosen the tooth from the gum and bone for enabling quick completion of the extraction using either a conventional dental forcep or plier or, in certain instances, extraction by the dental professionals fingers pinching and removing the pre-loosened tooth.

The present invention is further an improvement over prior art dental appliances (pliers and/or forceps) in the design of an intentional offset or misalignment established between a forward most extending and pointed beak associated with a first handle (applied against an inside or lingual surface of the tooth) and a spatially opposing and crosswise extending pad support which is adapted to seat against an outside (or buccal) surface at or below the gum line and so that the pad does not directly contact or abut the tooth. Upon establishing the above positioning of the beak and pad support, the handles are supported by the user such that they are maintained in a static position relative one another (i.e. are not clamped or pinched together once the beak and pad support are pre-positioned) and the appliance pivotally outwardly rotated in a lever-style fashion to effectuate smooth and easy separation (or "pop") of the decayed tooth from the bone.

The configuration of the dental pliers appliance in one particular configuration is further such that the offset pad support defines a center point of rotation proximate an edge location just below the patient's gum line. During combined outwardly and downwardly actuated rotation of the handles, the tooth is caused to pivot forwardly and forcibly dislodge from the gum line and bone and due to the configuration and positioning of the pointed jaw portion and offsetting support. This misalignment results in a greater and more efficient rotating force (and as opposed to a conventional pulling or withdrawing force) capable of being exerted directly upon the tooth and in order to quickly and efficiently loosen the root connections of the tooth within the jawbone and without inflicting of damage to the patient's dental bridge.

As will be described in more detail in the ensuring description the configuration of the handles, with associated beak and pad support, varies between a first variant suited for removing teeth projecting from and along a lower gum line and jaw bone of a patient and a second variant likewise suited for removing teeth projecting from and along an upper gum line (further including without limitation such as a pair of upper appliances exhibiting mirrored configurations for use with either of right/left quadrants of the upper bridge for engaging and dislodging teeth extending along respective halves of the upper gum line.

Additional features of the dental pliers appliance include the ability of the appliance to successfully engage and dislodge broken or fractured teeth (root tips), such as which in particular exhibit very little tooth mass extending at or above the gum line and despite having an embedded root tip. Additional features include a sanitary, typically flexible and plasticized, cap attachment which is capable of being releasably secured over the configured support during such positioning of the support along the patient's gum line. An associated method for loosening teeth prior to subsequent lineal extraction is also disclosed utilizing the above structure.

BRIEF DESCRIPTION OF THE DRAWINGS

Reference will now be made to the attached drawings, when read in combination with the following detailed description, wherein like reference numerals refer to like parts throughout the several views, and in which.

DETAILED DESCRIPTION OF THE PREFERRED EMBODIMENTS

Figure 2:
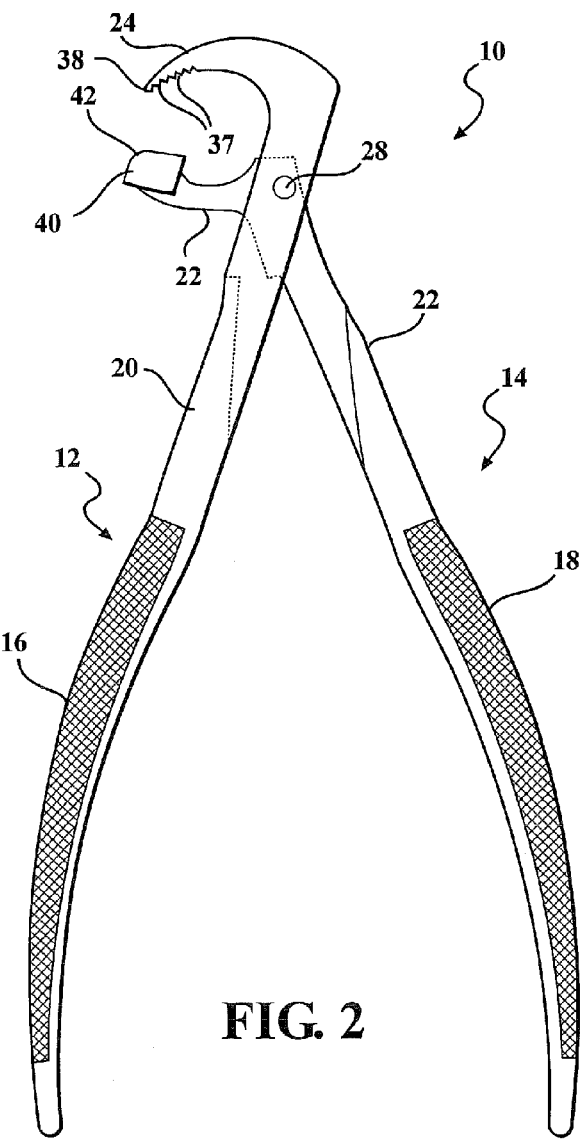
FIG. 2 is a plan view of a first variant of the dental pliers according to a first variant for use in removing teeth located within a patient's lower jaw and according to the present invention.

Referring now to FIG. 2, a pair of dental pliers is illustrated at 10 according to a first preferred variant of the present invention for use in loosening teeth located along a lower jaw line of a patient. As discussed previously, the dental appliances according to any of the design variants disclosed herein is an improvement over prior art dental pliers and forceps in that it facilitates providing an outward directed and rotating force, rather than a pulling force, applied to a selected tooth and in order to more quickly and efficiently loosen the interface between the tooth root from the patient's gum line and bone.

As further described, the present invention is an improvement over prior art dental appliances (pliers and/or forceps) in that the intentional offset or misalignment of the jaw and the pad (or support) allows a greater and more efficient rotating force (and as opposed to a conventional pulling or withdrawing force) to be exerted directly upon the tooth, such as at a location below the patient's gum line, and in order to quickly and efficiently remove the tooth without any damage to the patient's dental bridge.

Figure 3:
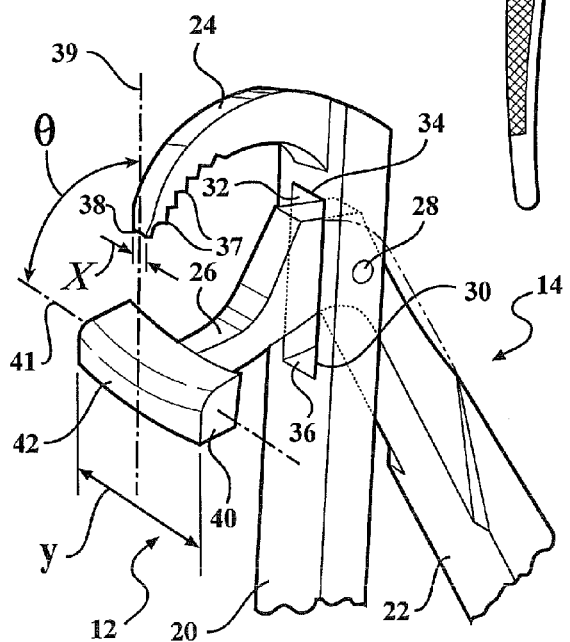
FIG. 3 is an enlarged and sectional perspective view of the dental pliers tool according to FIG. 1 and which further illustrates the jaw and support according to the present invention.

Referring again to FIG. 2 as well as to FIG. 3, the dental pliers 10 (also interchangeably termed dental forceps or dental appliance) is constructed in one non-limiting variant of a medical grade steel and includes a first handle 12 and second pivotally connected handle 14. Each of the handles 12 and 14 include extending and configured user grasping portions, see at 16 and 18, respectively, as well as associated intermediate portions 20 and 22 and terminating portions 24 and 26. In the particular instance of the variant of FIGS. 1 and 2, the configuration of the dental pliers appliance 10 illustrated is specifically suited for the dislodging and removal of teeth located along a lower gum line and jaw bone of a patient.

The handles 12 and 14 are further hingedly interconnected at pivot point 28 such that the terminating portions 24 and 26 extend forwardly of the pivot point 28 and are pivotally associated relative to one another based upon the manipulated pivotal orientation of the handles 12 and 14. In one non-limiting variant, an aperture is defined along and within the first handle 12, and such as is best illustrated in FIG. 3 by inwardly facing side walls 30 and 32 and interconnecting end walls 34 and 36 which define an elongated and rectangular slot shaped aperture.

As shown in FIG. 3, the aperture in the first handle 12 is located in proximity to its terminating portion 24, such that the second handle 14 pivotally intersects at a point extending through the aperture. A pin (again defined by pivot point 28) extends crosswise through the intersecting location of the first and second handles 12 and 14 to define the pivotal connection. It is further understood that both the configuration of gripping portions of the handles, as well as the manner in which the handles are pivotally connected together (and such as in the overlapping pivotal mounting arrangement depicted in succeeding embodiments) may be modified without departing from the scope of the invention.

Referring again to FIGS. 2 and 3, the terminating portion 24 associated with first handle 12 exhibits an arcuately/downwardly extending and substantially pointed beak 38. The beak 38 may optionally exhibit a plurality of serrated surfaces 37, such as which are depicted along its inner edge.

In contrast, the second terminating portion 26 (associated with second handle 14) concludes in a three-dimensional and crosswise directional extending pad-shaped support 40 exhibiting an ergonomically configured and supporting surface 42 which is designed to substantially match that of the patient's gum line. The pad support 40 and surface 42 as shown is arranged in a spatially opposing relationship relative to the curved beak 38.

Figure 4:
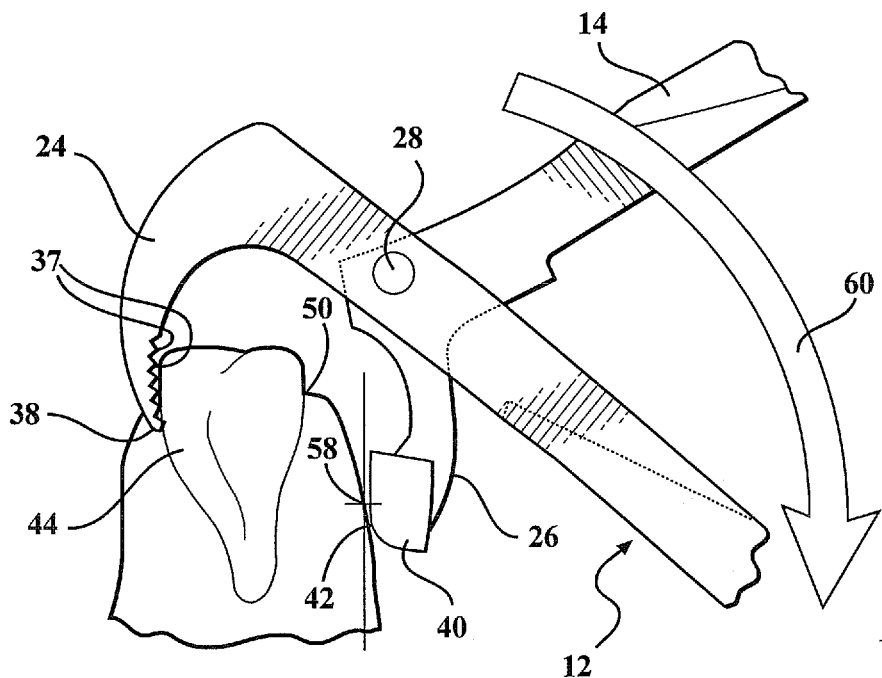
FIG. 4 is an illustration, of a nature similar to that shown in FIG. 1, and showing the tool according to FIGS. 2 and 3 in a first engaged position relative a patient's tooth located along the bottom jaw.

As further shown in FIG. 3, the pointed beak 38 exhibits a fairly small surface contacting dimension "x" and which typically is exhibited by a fairly narrow knife edge configured for engaging the lingual tooth surface at a location at or beneath the gum line (FIG. 4). In relation, a much larger crosswise dimension is depicted at "y" and which is associated with the cross wise extending dimension of the pad support surface 42.

Without limitation, the crosswise extending dimension "y" of the pad support surface 42 (and which is further identified in FIG. 3 as any lateral or crosswise extending distance of the surface 42 greater than that of the beak 38 and its knife edge relative to a vertical/perpendicular extending cutaway, see at 39) extends through the terminating portion 24 and beak 38. Accordingly, and by this definition, the dimension "y" is defined as having any component of length greater than either lateral end point of the smaller beak (knife edge) dimension "x", again for any angle θ established between the lineal cutaways 39 (extending through a center line associated with a longest lineal dimension of the beak 38) and again at 41 (extending through a center line associated with a longest crosswise extending dimension of the pad support 40).

The pad support 40 and associated conforming surface 42 can also exhibit a crosswise axis 41 which establishes any desired angle θ (again FIG. 3) relative to the crosswise extending dimension (such as not limited to the substantially perpendicular arrangement depicted in FIG. 3 in relation to the standard lower appliance) and further which can be any multiple larger in dimension than the smaller "x" dimension associated with the narrowed beak 38. In this manner, the pad 40 and surface 42 provides adequate buccal support during the necessary rotating/lever induced loosening of the tooth and its root tips exerted narrower and sharper edge of the beak 38 relative to the underlying bone structure in the dental bridge.

It is further noted that the pad 40 with conforming support surface 42 is anchored to the forward end of the terminating portion 26 and which in turn extends forwardly of the pivot point 28. In this manner, the pad support with bridge conforming surface 42 is constructed such that it provides constant support against the buccal surface of the jawbone bridge exterior at or below the gum line and which, during outward rotating or lever action exerted on the handles, causes the partially embedded beak 38 to exert against the lingual surface of the tooth (see for example at 44 in FIG. 4) in order to break the tooth and its roots free from the surrounding bone structure (known in the relevant technical art as "popping" the tooth loose from the bone), such as again prior to subsequent linear extraction of the now loosened and easily removable tooth.

Figure 1:
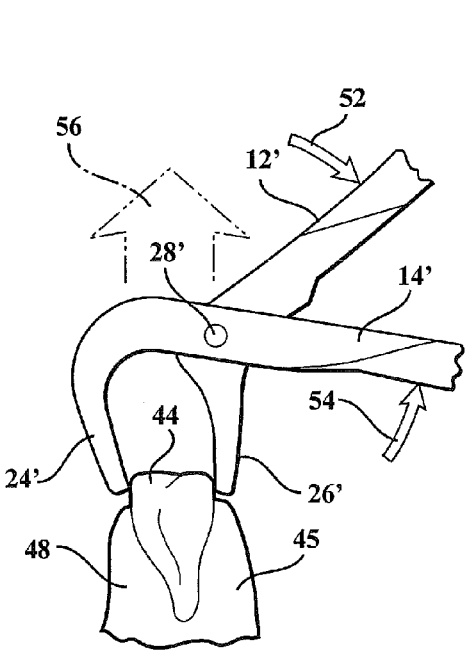
FIG. 1 is an illustration of a conventional plier design according to the Prior Art and illustrating the previously known manner of withdrawing teeth utilizing a pulling or withdrawing force.

In comparison, and as is further shown in FIG. 1, the prior art technique for removing a selected tooth 44 from its associated gum 46 and bone 48 contemplates the opposing jaw portions, see again 24' and 26', engaging opposite facing sides of the tooth 44, above a gum line 50 from which the tooth 44 projects. Upon positioning of the prior art pliers device in the position illustrated in FIG. 3, and further upon the handles 12' and 14' being compressed in the directions illustrated at 52 and 54, respectively, a further pulling force (referenced by directional arrow 56) is concurrently applied in a direction opposite that of the holding force established between the tooth 44 and the patient's gum 46 and bone 48.

While eventually effective in removing the patient's tooth 44, it has been found that the prior art application of FIG. 3 results in both the requirement of extensive time and effort necessary to successfully dislodge the tooth, this having a commensurate effect on the patient's comfort level as well as increasing the likelihood of the tooth, and in particular the embedded root tip, becoming fractured or broken off during the removal process. The prior art tool and application of FIG. 1 has also been found more likely to cause damage to the bone and gums which may have otherwise been avoided in the absence of the dental service provider not having to exert the necessary pulling force in order to remove the tooth.

Referring again to FIGS. 4 and 5, first engagement and second actuating positions are again illustrated in reference to the dental appliance tool and method of operation according to the present invention. In particular, and referencing first FIG. 4, the pad support 40, again with ergonomic and contoured surface 42, is illustrated in position along a selected location of the patient's gum 46 and below the gum line 50.

Upon further aligning of the opposing and pointed jaw 38 in abutting fashion against an inwardly facing side of the tooth, again shown at 44 and such that the pointed edge projects a distance between and below the adjoining gum line and tooth and with the serrated edge 39 located against the inwardly facing edge of the tooth 44, the offset support 40 defines a center point of rotation 58 proximate an edge location of the gum line 46 and bone 48. The handles 12 and 14 are then initiated in a rotating direction in an outward fashion away from the patient's gum line 46, and as illustrated by directional arrow 60.

Figure 5:
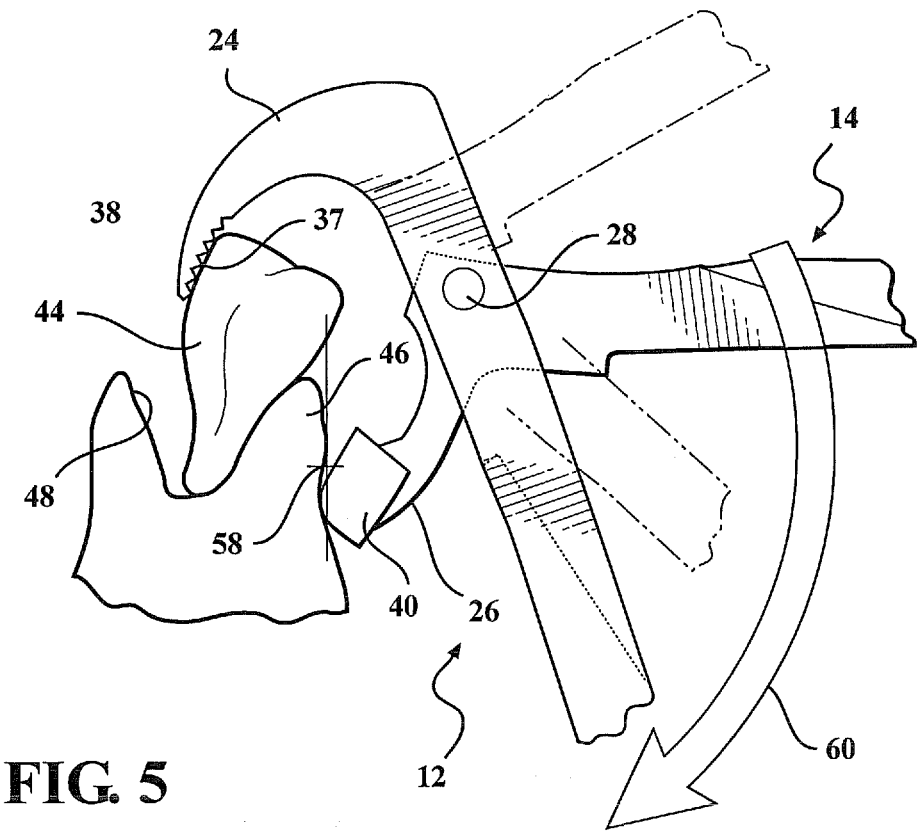
FIG. 5 is an illustration of a furthering removal or cantilevered position of the tooth and in which the tool, also shown in FIG. 4, is rotated resulting in the tooth being forcibly dislodged or loosened from the root interface with the patient's lower bridge (bone) and gum line.

Referring further to FIG. 5, continued rotation of the handles 12 and 14 along the direction of arrow 62 causes a cantilever or dislodging force to be applied to the tooth 44, about the center point of rotation 58, and so that the tooth 44 is caused to be forcibly dislodged, along the gum line 50, and from the patient's gum 46 and associated bone 48. Of significant advantage is the ability to apply a single and multiplied rotating and cantilevering force to the dental pliers appliance, and which is measured by the offsetting distance between the edge of the jaw 38 and the center point of rotation 58 established by the support 40. The ability to apply such a combined and unidirectional rotating force causes the tooth 44 to be much more quickly dislodged or separated from the underlying bone interface for subsequent lineal extraction than in the instances of the prior art in which extraction through application alone of grasping forces 52 and 54 tends to cancel out a significant degree of the pulling/withdrawing force 56 (see again FIG. 1) and by which no effective cantilevering or rotating forces are created to assist in tooth removal.

Figures 6, 7, 8:
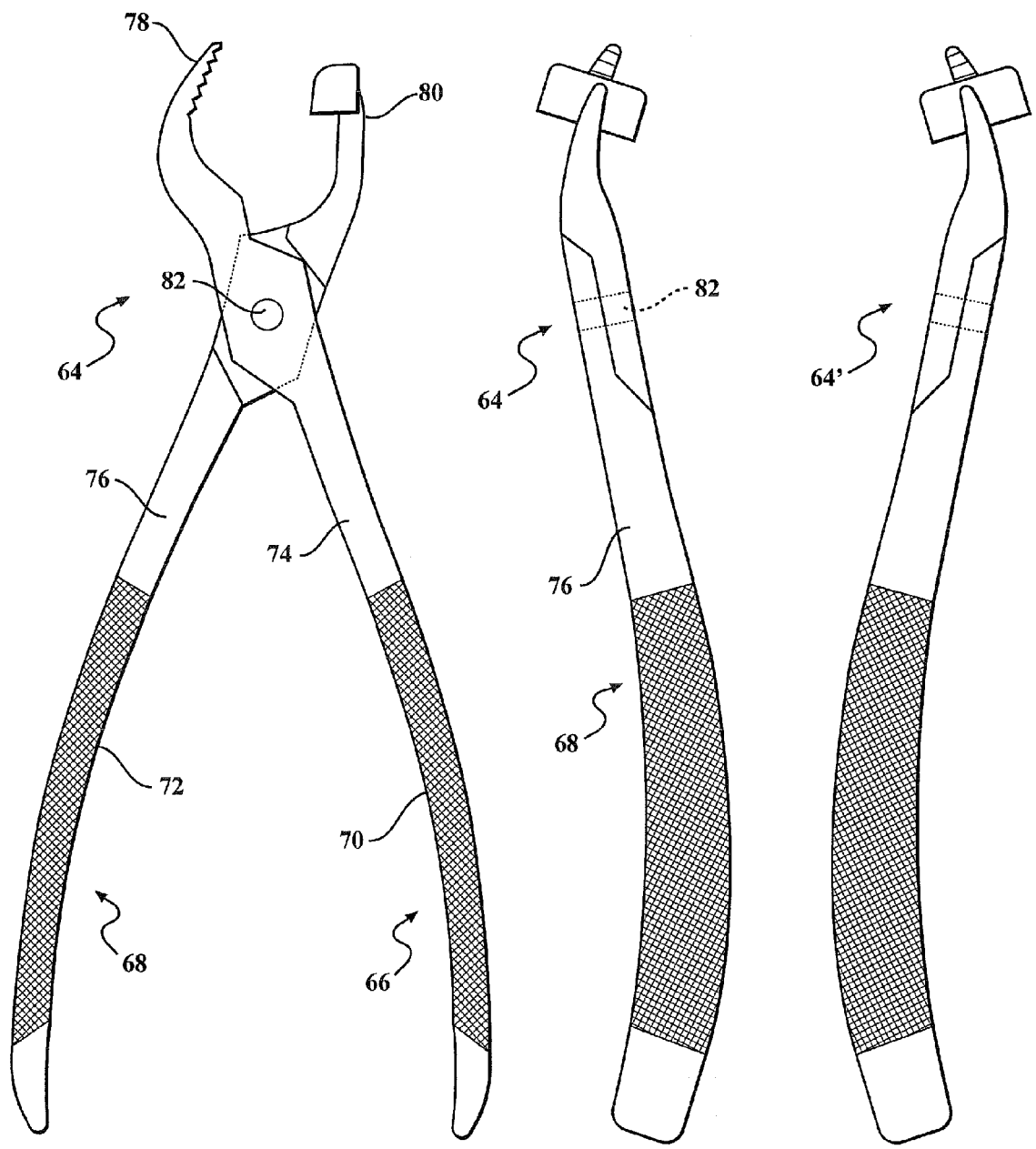
FIG. 6 is plan view of a second variant of the dental pliers tool for use in removing teeth located along a first half of a patient's upper jaw and according to the present invention.
FIG. 7 is a side view of the dental pliers tool illustrated in FIG. 6 and according to the present invention.
FIG. 8 is a side view of an opposite and minor image dental pliers tool, with respect to that illustrated in FIGS. 6 and 7, and which is used for removing teeth located along a second half of a patient's upper jaw.

Referring now to FIGS. 6 and 7, plan and side views are illustrated, respectively, of a second variant 64 of a dental pliers appliance for use in removing teeth according to the present invention. In particular the variant 64 of FIGS. 6 and 7, and as will be further explained in reference to FIGS. 10 and 11, is suited for removing teeth located along a patient's upper jaw and gum line.

The features of the dental pliers appliance 64 are essentially the same as those associated with the variant 10 illustrated in FIGS. 2 and 3 and again include handles 66 and 68 with grasping portions 70 and 72, intermediate extending portions 74 and 76, and configured and opposing terminating portions 78 and 80. The appliance 64 further includes a pivotal connection 82 constructed by reduced section and overlapping portions (see in particular FIG. 7), of each of the intermediate extending portions 74 and 76, and through which is inserted a pin (not shown).

Figure 9:
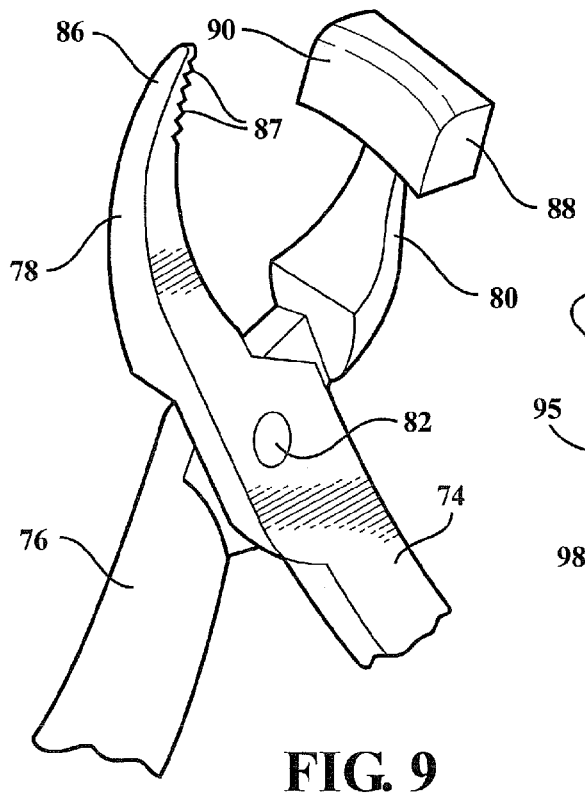
FIG. 9 is an enlarged and sectional perspective view of the dental pliers tool according to the upper jaw variant of FIG. 8 and which further illustrates the jaw and support according to the present invention.

As also shown in FIG. 9, the terminating portion 78 is again provided with a pointed and angled jaw 86 (with inner and serrated surfaces 87) and the terminating portion 80 as a pad-shaped support 88 with ergonomically configured surface 90. Referring further to FIGS. 10 and 11, engagement and removal positions are illustrated of the appliance 64 in relation to a tooth 92 located within an upper gum 94 and bone 96 of a patient. Also illustrated in FIGS. 10 and 11 at line 95 is a breakaway location and by which a fractured root tip (such as resulting from an unsuccessful tooth removal procedure) remains embedded in the patient's gum line and bone. As will be described, the pliers device of the present invention is effective in removing root tips as well as complete (undamaged) teeth.

Figure 10:
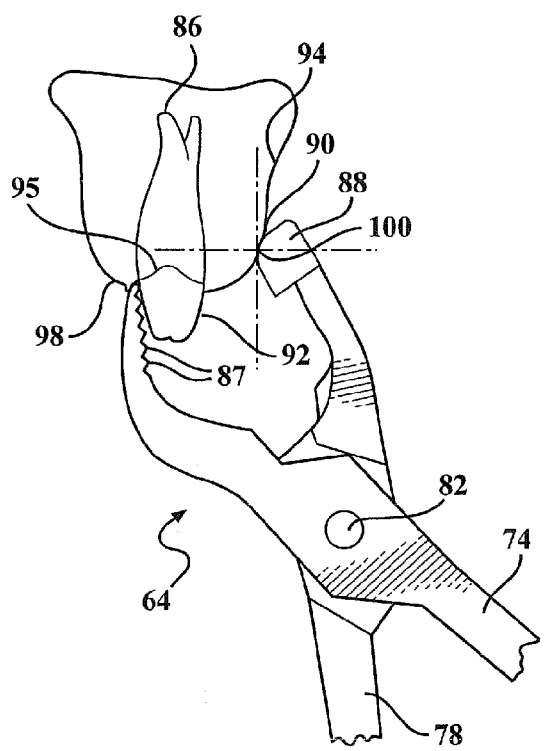
FIG. 10 is an illustration, of a nature similar to that previously shown in FIG. 4, and showing the tool according to either of the sub-variants of FIGS. 7 and 8, in a first engaged position relative a patient's tooth located along a selected half of the upper jaw.
Figure 11:
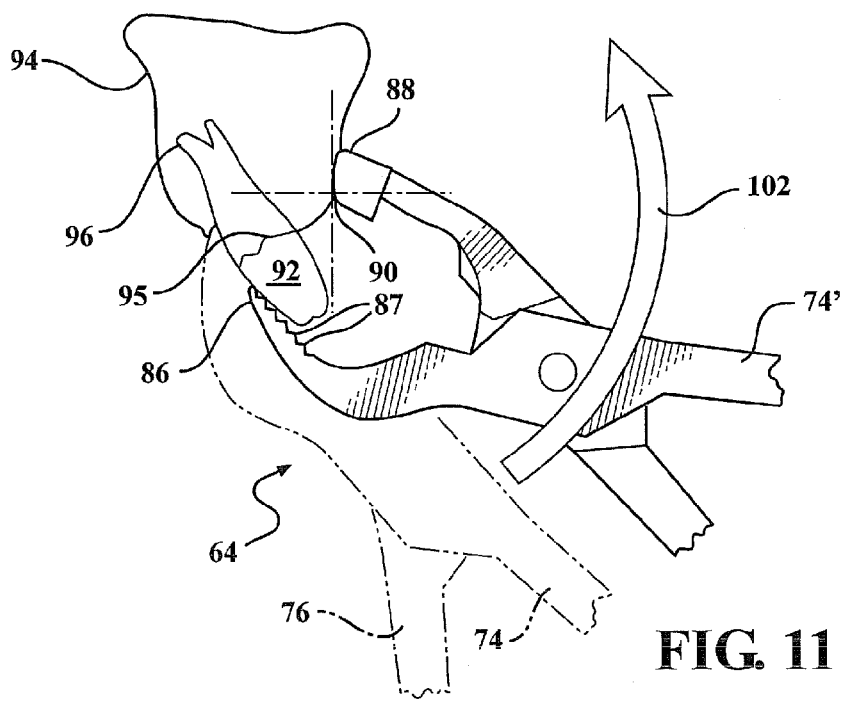
FIG. 11 is an illustration of a furthering removal or cantilevered position of the tooth and in which the tool, also shown in FIG. 10, is rotated resulting in the tooth being forcibly dislodged or loosened from the patient's upper bridge and gum line.

As illustrated in the initial engagement position of FIG. 10, the support 88 with ergonomic surface 90 is positioned against the gum 94, at a position above in this instance the patient's upper jaw gum line 98. At the same time, the angled jaw 86 is again abutted against an inwardly facing side of the tooth 92 (again a recessed distance above the gum line 98 and such that the optionally depicted and inwardly serrated surface 87 grips the corresponding inner surface of the teeth) in order to define a center point of rotation 100 of the support 88 and which is offset the desired distance from the jaw 86 and the upper gum line 98.

Referring to FIG. 11, a rotating and cantilevering force is applied along the handles of the appliance 64, in the direction of arrow 102 (from initial positions designated by handles 74 and 76 to angularly displaced positions 74' and 76'), and so that the selected upper tooth 92 is likewise rotated and forcibly loosened from the gum 94 and bone 96 defining the patient's upper bridge. The same forces of physics apply in the upper jaw variant 64 of the appliance, as compared to those illustrated and described in reference to the lower jaw appliance 10 in FIGS. 4 and 5, and by which the rotating and cantilevering forces about the center point of rotation effectively and efficiently actuate and loosen the tooth, such as in order to more easily linearly extract the tooth with a minimum of time and effort.

Referring to FIG. 8, a side view of an opposite and mirror image dental pliers tool, see at 64', is illustrated and with respect to that illustrated at 64 in FIGS. 6 and 7. In particular, the tool 64' is an identically constructed, albeit again mirrored image configuration, of the variant 64 and for the specific purpose of removing teeth located along a selected and second half of a patient's upper jaw. In comparison, the variant 64 is suited for removing teeth from a first upper extending half of the patient's jaw and the particular ergonomic configuration of either of the appliance variants 64 or 64', when viewed in side profile, is depending upon that which is easiest to grasp and manipulate during the engaging and dislodging procedure. The mirrored image sub-variant 64' is otherwise identically constructed as that illustrated at 64 such that a repetitive description of its elements is not required.

Figure 12:
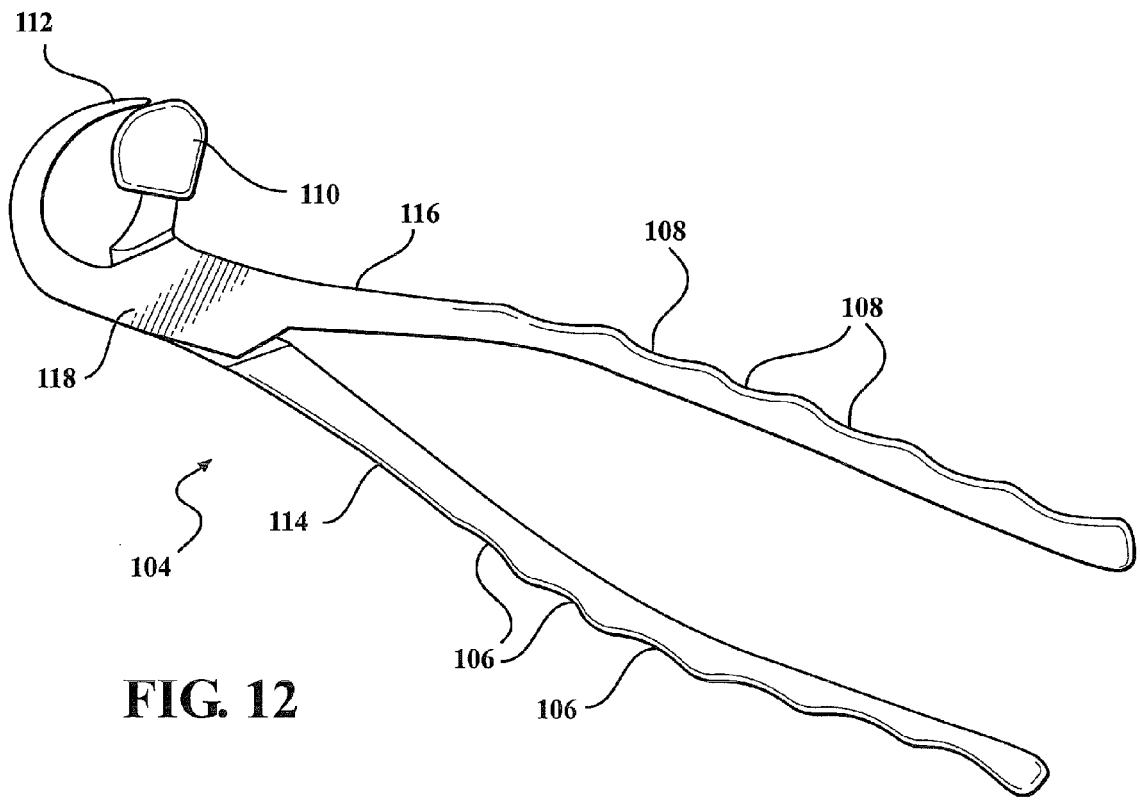
FIG. 12 is a plan view of a standard lower dental appliance according to the present inventions and which depicts such features as exterior handle fenestrations and sanitary cap for attachment over the pad support.

FIG. 12 is a plan view generally shown at 104 of a standard lower dental appliance according to another non-limiting example of the present inventions and which depicts such features as exterior handle fenestrations, at 106 and 108 for respective first and second handles. Other features include a sanitary cap 110 for attachment over the pad support in opposing and arrayed fashion relative to the pivotally actuating beak 112. As further depicted, the handles referenced at 114 and 116 exhibit flattened conforming portions at an inter-pivotal interface (with selected portion 118 being depicted in plan view in integrally extending fashion relative selected handle 116), and so that a pin or other pivotal fastening component (hidden from view) enables the handles to be pivotally secured together in order to establish desired spatial arrangements between the arcuate beak 112 and opposing pad support (covered by cap 110).

Figure 13:
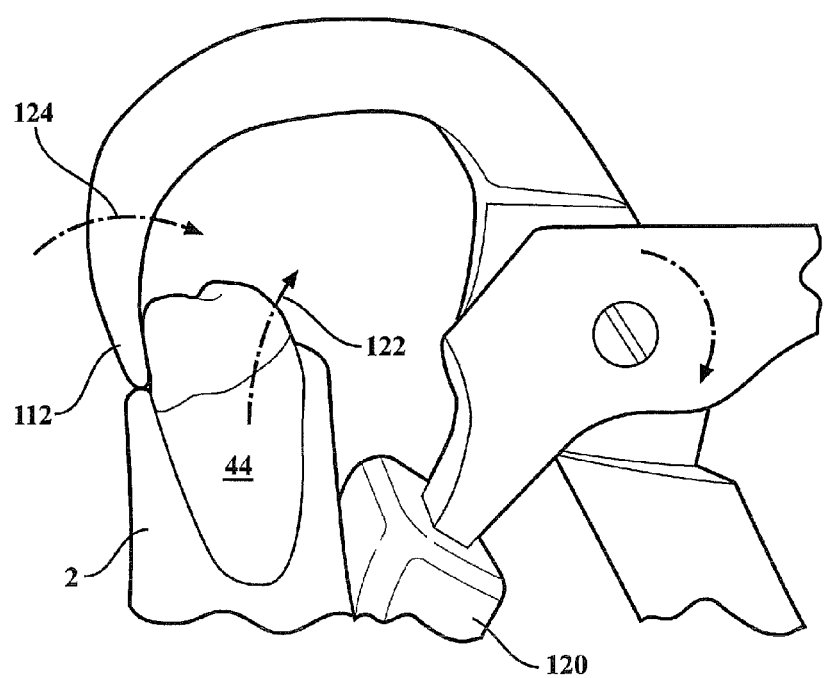
FIG. 13 is an enlarged environmental view of the beak and pad support associated with the dental appliance shown in FIG. 12 and illustrating their pre-positioning of the beak against the inner lingual surface of the tooth and the pad support supporting against the outer buccal surface below the gum line.

FIG. 13 is an enlarged environmental view of the beak 112 and pad support, at 120, associated with a dental appliance similar to as shown in FIG. 12. Pre-positioning of the beak 112 against the inner lingual surface of the tooth 44, as well as positioning of the pad support 120 against the outer buccal surface below the gum line 50, is best shown by this illustration and which facilitates a combined linear and rotating exerting force applied to the tooth (see arrow 122) upon simultaneous rotating/lever style force exerted by the beak (see further arrow 124). In this manner, the tooth and associated root tips are exerted away from the underlying bone structure of the jaw bone or bridge (see as designated at 2 in FIG. 13) and upon "popping" loose are very easily and subsequently linearly extracted such as again without limitation through the use of any conventional linear extraction tool.

Figure 14A:
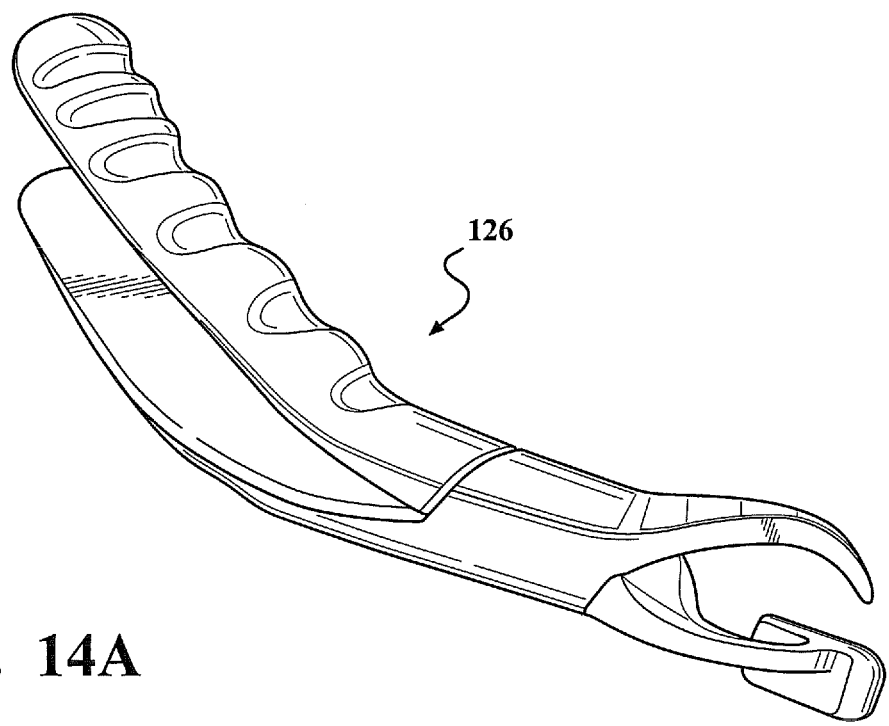
FIGS. 14A and 14B illustrate a pair of upper configured appliances adaptable for use with first and second upper quadrants of the patient's bridge.
Figure 14B:
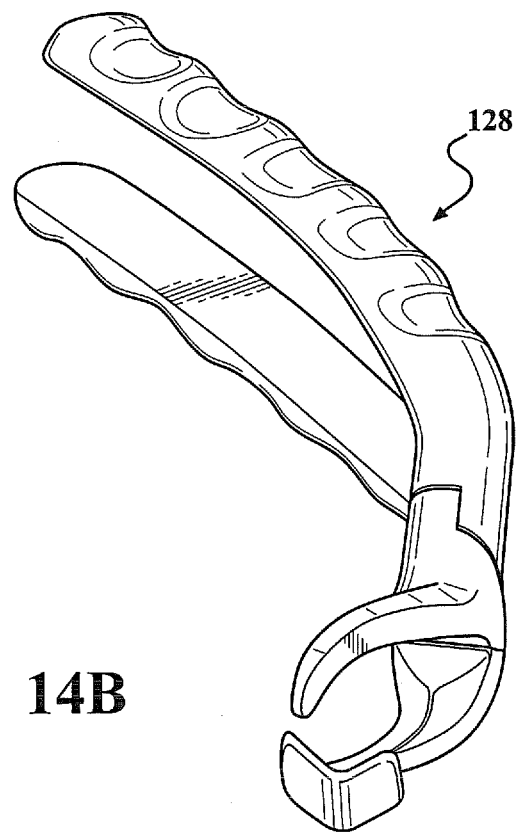

Finally, FIGS. 14A and 14B illustrate a pair of upper configured appliances 126 and 128 respectively and which are adaptable for use with first and second upper quadrants of the patient's bridge. Otherwise, the appliances 126 and 128 are structurally consistent in both construction and operation relative to the lower appliance 104 of FIG. 12, as well as the upper and lower appliance described in the preceding embodiments.

As previously described, a method is disclosed for pre-loosening teeth for subsequent linear extraction from a dental patient's gum line and bone using the dental appliance tool of the present invention and includes the steps of positioning a pad support along a buccal surface location at or below the gum line, concurrently positioning an opposing and pivotally adjustable beak of the appliance against a lingual side of a selected tooth projecting from the gum line, and while retaining the first and second pivotally secured handles in a static or fixed angular inter-relationship. The handles are then rotated in an outward fashion away from the patient's gum line, resulting in the separation of the root from the underlying bone, following which the tooth is subsequently linearly extracted from the patient's gum line and bone.

Additional steps of the present method include offsetting the beak from the pad support such that a surface of the pad support defines a center point of rotation proximate an edge location of the gum line, as well as ergonomically configuring the first terminating portion to substantially match that of the patient's gum. Yet additional steps include configuring the second terminating portion with a substantially pointed end, as well as configuring the dental pliers appliance to engage and dislodge a tooth located along either the lower or upper gum line and associated jaw bone of a patient. Still further method steps include angling a side profile of the first and second pivotally connected handles, according to either upper jaw sub-variant of the appliance, as well as again releasably securing a plasticized and sterilized cap attachment over the ergonomically configured and first terminating portion.

Having described my invention, additional preferred embodiments will become apparent to those skilled in the art to which it pertains and without deviating from the scope of the appended claims.

The invention claimed is:

1. A dental pliers appliance for loosening a tooth from a patient's gum line and bone through the application of a rotating motion, said appliance comprising:
   first and second handles pivotally connected at intermediate locations, each of said handles having a user grasping portion;
   said first handle terminating forward of said pivotal connection in a beak extending in an arcuate fashion along its extending length and defining an inner curved surface terminating in an end most located narrowed blade edge extending an "x" dimension relative to a centerline axis extending through said arcuate beak;
   said second handle terminating in a pad support opposing said beak and extending blade edge, a contoured surface of said pad support exhibiting a crosswise extending dimension "y" extending along a longest dimension associated with said pad support, said "y" dimension being larger than said "x" dimension; and
   said beak and extending blade edge adapted to engage a surface of the tooth in combination with said pad support adapted to being applied along a surface of the patient's gum line below that same tooth, following which rotation of said appliance exerting an end most portion of said inner curved surface of said beak against the tooth in order to separate the tooth and its roots from the underlying bone.

2. The dental pliers appliance according to claim 1, said pad support defining a center point of rotation proximate and below an edge location of a gum line and bone associated with a given tooth.

3. The dental pliers appliance according to claim 1, further comprising said first and second handles exhibiting an angled side profile such that said appliance is configured for engaging and dislodging a selected tooth located along an upper gum line and jaw bone of a patient.

4. The dental pliers appliance according to claim 3, said first and second handles further comprising at least one of first and second angled and mirrored side profiles for use along corresponding first and second halves of the patient's upper jaw.

5. The dental pliers appliance according to claim 1, said appliance having a specified shape and size and being configured for engaging and dislodging a fragmented tooth and associated root tip.

* * * * *